(12) United States Patent
Mercier et al.

(10) Patent No.: US 10,842,404 B2
(45) Date of Patent: Nov. 24, 2020

(54) ELECTRODE, WEARABLE ASSEMBLY AND SYSTEM

(71) Applicant: DREEM, Paris (FR)

(72) Inventors: Hugo Mercier, Paris (FR); Quentin Soulet de Brugiere, Paris (FR); Pierre Emerich, Paris (FR); Martin Herrera, Boulogne-Billancourt (FR); Camille Kerbaul, Paris (FR); Hsin-Yin Chiang, Paris (FR)

(73) Assignee: DREEM, Paris (FR)

( * ) Notice: Subject to any disclaimer, the term of this patent is extended or adjusted under 35 U.S.C. 154(b) by 85 days.

(21) Appl. No.: 16/006,172

(22) Filed: Jun. 12, 2018

(65) Prior Publication Data

US 2018/0353096 A1 Dec. 13, 2018

(30) Foreign Application Priority Data

Jun. 12, 2017 (EP) .................................... 17305713

(51) Int. Cl.
*A61B 5/0478* (2006.01)
*A61B 5/00* (2006.01)

(52) U.S. Cl.
CPC .......... *A61B 5/0478* (2013.01); *A61B 5/6835* (2013.01); *A61B 5/6803* (2013.01); *A61B 2562/0215* (2017.08)

(58) Field of Classification Search
CPC ... A61B 5/0478; A61B 5/6814; A61B 5/6835; A61B 2562/0215
See application file for complete search history.

(56) References Cited

U.S. PATENT DOCUMENTS

| | | | |
|---|---|---|---|
| 9,314,183 B2 * | 4/2016 | Chi ...................... | A61B 5/6803 |
| 9,668,694 B2 * | 6/2017 | Badower .............. | A61B 5/0476 |
| 9,907,482 B2 * | 3/2018 | Knight ................... | A61B 5/163 |
| 2008/0154112 A1 * | 6/2008 | Murphy ............... | A61B 5/0478 600/386 |
| 2015/0141788 A1 | 5/2015 | Chi et al. | |
| 2015/0282731 A1 | 10/2015 | Hill et al. | |

FOREIGN PATENT DOCUMENTS

| | | |
|---|---|---|
| CN | 104 799 853 A | 7/2015 |
| WO | 2017065196 A1 | 4/2017 |

* cited by examiner

*Primary Examiner* — Lee S Cohen
(74) *Attorney, Agent, or Firm* — Nixon & Vanderhye

(57) ABSTRACT

An electrode for acquiring electroencephalogram signals of a user includes a base and a plurality of legs extending from the base at first extremity. The legs include a second extremity covered with an electrically conductive material. The second extremity includes a smaller cross-section than the first extremity of the legs so the legs can penetrate through hair of the user. The legs elastically flex such that, when the electrode is applied on a user's head, the electrically conductive material of the second extremity contacts a scalp of the user, wherein the base is of cuboid shape having two side faces, the legs being directly attached to the side faces of the base, the legs being symmetrically attached to the base with respect to a longitudinal axis and the legs attached to a side face of the base facing the legs attached to the other side face of the base.

12 Claims, 5 Drawing Sheets

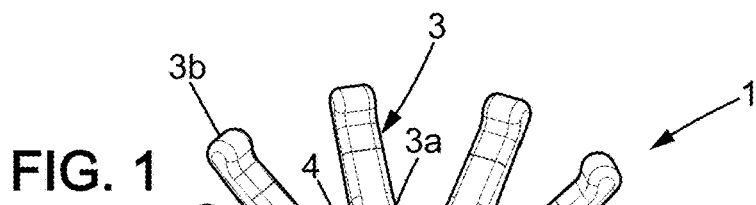
FIG. 1
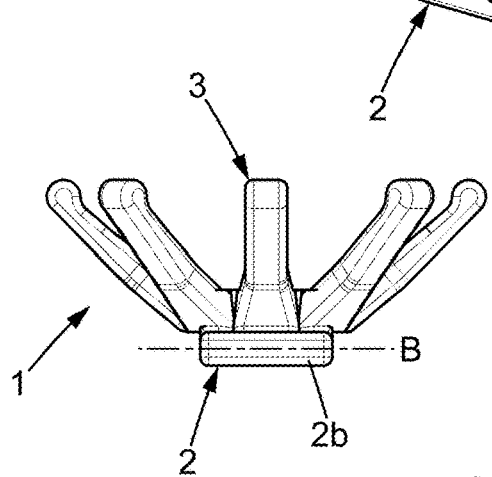
FIG. 2
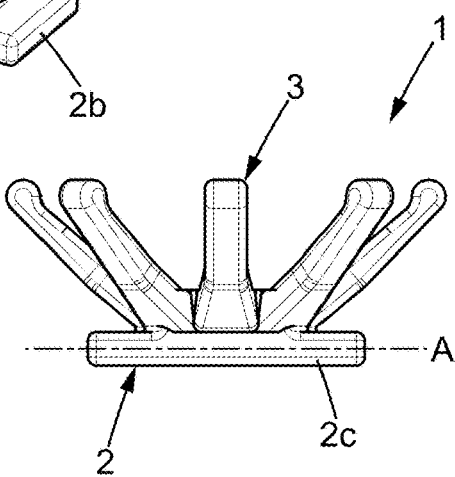
FIG. 3
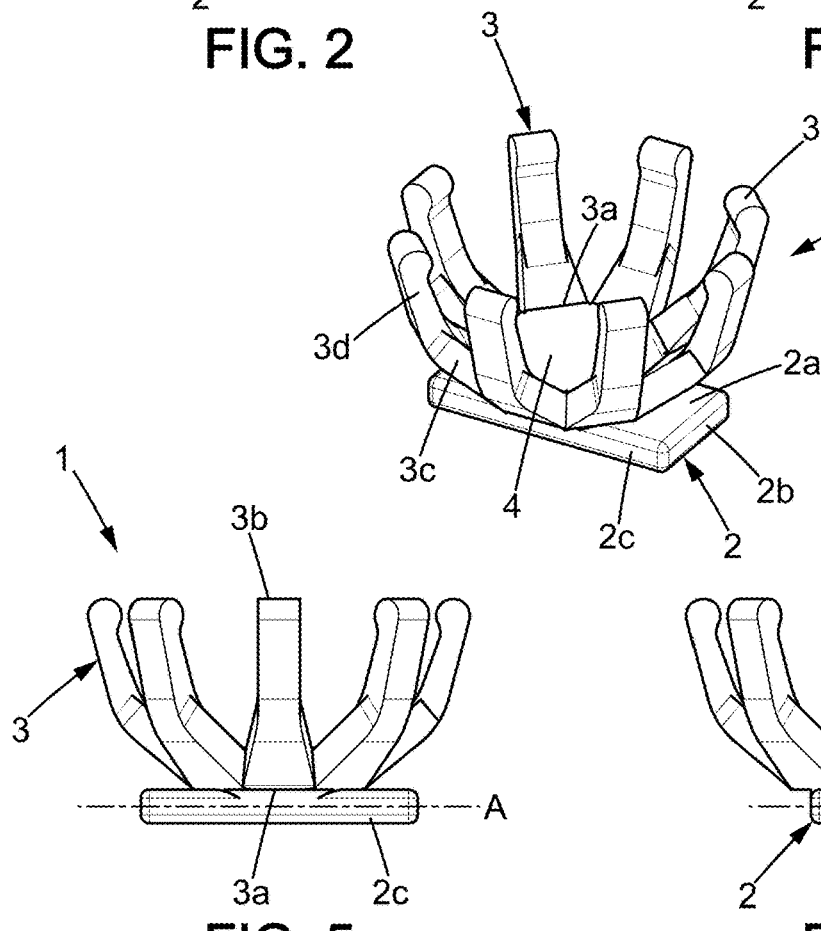
FIG. 4
FIG. 5
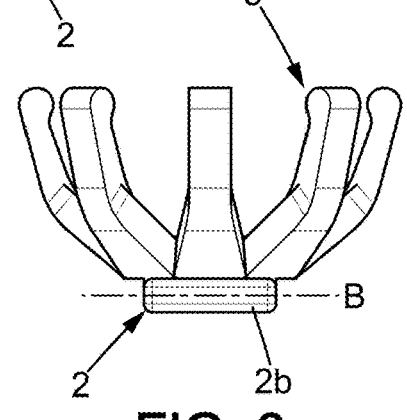
FIG. 6

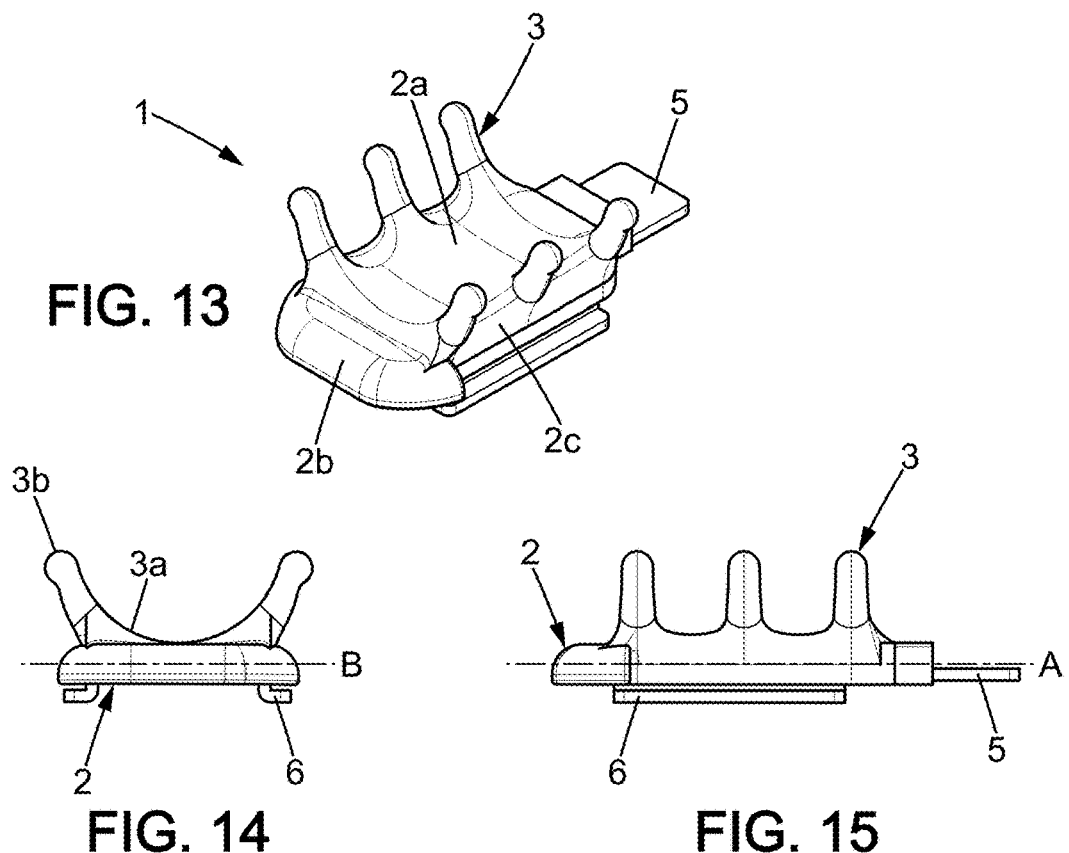
FIG. 13
FIG. 14
FIG. 15
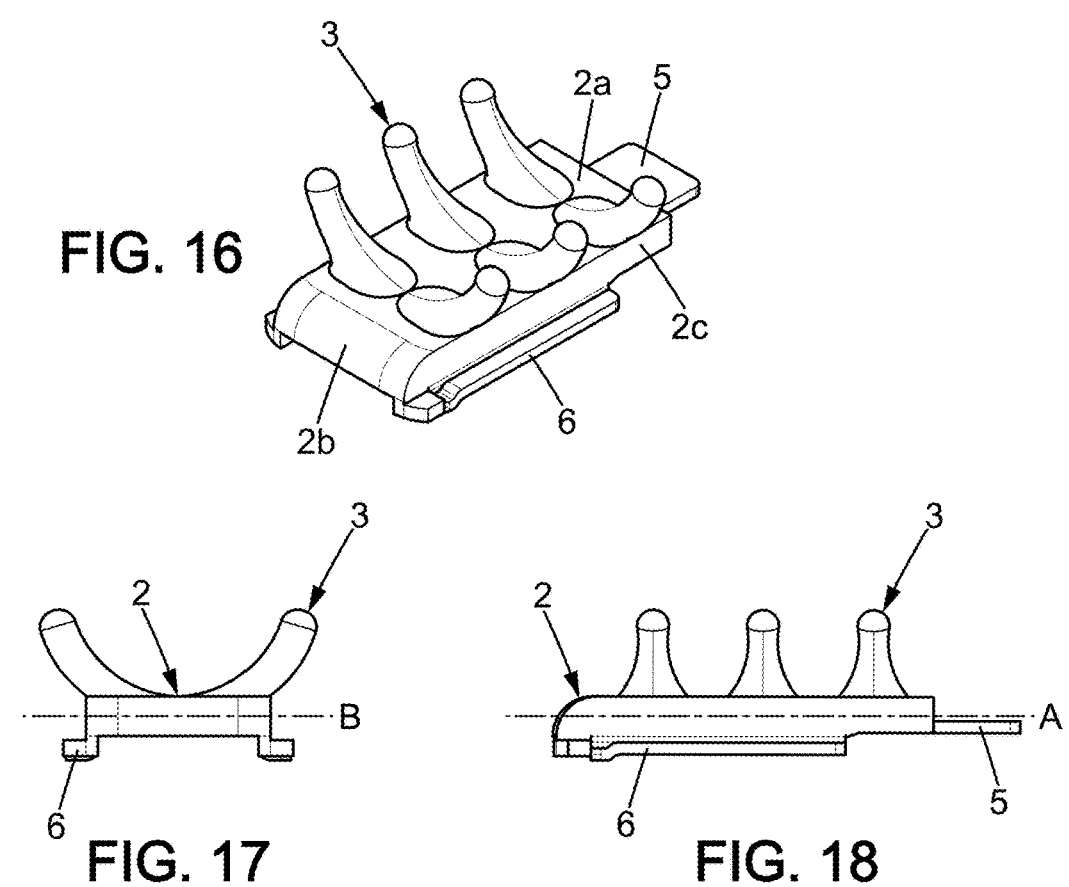
FIG. 16
FIG. 17
FIG. 18

ELECTRODE, WEARABLE ASSEMBLY AND SYSTEM

BACKGROUND OF THE INVENTION

Field of the Invention

The present invention relates to electrodes for measuring bioelectrical physiological signals, wearable assemblies comprising such an electrode and systems comprising a wearable assembly.

It more particularly relates to dry and non-invasive electrodes for measuring bioelectric physiological signals, such as electroencephalogram signals, during a period of sleep of a user.

Description of the Related Art

An electrode for measuring bioelectric physiological signals (or bio-signals) is used to detect and measure bio-signals, which for example represent a cerebral activity or a muscular activity.

Such bio-signals are for example used to make an electroencephalogram (or EEG), an electromyogram or an electrocardiogram.

Measuring bioelectrical physiological signals can have a variety of practical applications. For example, such electrodes are used in devices developed to analyze the cerebral activity of a user. This is generally performed during a medical examination of the user, for a short time. For some patients staying at the hospital, it may be used over a longer period of time. For example, such measurements may be performed during a whole night. Recently, measurements of bio signals were performed outside of a medical facility. This is because the users are more and more tending to monitor themselves. Occurrence of one such need is measurement of cerebral activity of the user outside a medical facility during his sleep. Such measurement of cerebral activity may be use in a purpose of reinforcing the beneficial effects of the sleep of the user. To measure the bio-signals, the electrodes generally have to be in contact with the skin of the user. In particular, to acquire bio-signals representing the cerebral activity of the user, the electrodes are in contact with the scalp of the user.

For some applications, wet electrodes can be used. Conventional wet electrodes include a disc made of a conductive material, a wet conductive gel used to establish an electrical connection through any hair between the skin of the user and the conductive disc. However, the use of a gel in combination with the need of skin preparation is time consuming for a user to set up and irritating and uncomfortable for the subject, especially for a nightly use in a period of sleep outside a medical facility.

In response, dry electrodes, which do not require conductive gels or skin preparation, have been explored as an alternative. In practice, dry electrodes suffer from numerous usability issues. Although acquiring signals on bare skin, for example the forehead of the user, is relatively easy, most EEG setups also require electrodes on areas of the head covered by hair, for example at the back of the head.

Patches of hair, depending on the thickness, are often difficult to penetrate and they may block the electrode from directly reaching the skin, and then involve difficulty of acquiring rugged bio-signals.

Known from prior art, such electrodes typically comprise straight, hard fingers designed to push through the hair to the scalp. Although these electrodes may reach the scalp and then may be able to measure a rugged bio-signal, the straight hard fingers may also involve discomfort and pain due to the pressure applied by the fingers to the scalp of the user.

Actually, there is no electrode that is capable of acquiring a rugged-signal for EEG setups and being enough comfortable to be worn daily by a user during a period of sleep.

The present invention aims at improving the situation.

SUMMARY OF THE INVENTION

In a first aspect, the present invention relates to an electrode for acquiring electroencephalogram signals of a user, comprising a base and a plurality of legs extending from said base at first extremity, said legs comprising a second extremity covered with an electrically conductive material, said second extremity comprising a smaller cross-section than the first extremity of said legs such that the legs are able to penetrate through hair of the user and wherein the legs are able to elastically flex such that, when the electrode is applied on a user's head, the electrically conductive material of the second extremity is in contact with a scalp of the user.

The particular geometry of the legs allows the electrode to be in contact with the scalp of the user, since the small diameter at the extremity of the legs allows the legs to slide through the hair of the user. The larger diameter at the other extremity of the legs enhances the rigidity of the legs such that the second extremity of the legs is in contact with the scalp of the user. Moreover, the pressure applied to the electrode against the scalp is for the most absorbed by the base, which render the electrode comfortable.

In another aspect, the legs extend from the support such that said legs form an angle with a first longitudinal face of said support.

In another aspect, the plurality of legs comprises between three and eight legs.

In another aspect, the legs are disposed symmetrically with respect to a longitudinal axis of the base.

In another aspect, the legs are disposed symmetrically with respect to a transversal axis of the base.

In another aspect, at least one leg, optionally each leg forms an angle comprised between 20° and 80° with the first longitudinal face of the base, more particularly between 20° and 60°.

In another aspect, the electrically conductive material comprises a mixture of silver and silver chloride.

In another aspect, the legs are made of electrically conductive material, in particular a conductive high consistency silicone rubber.

In another aspect, the base is made of electrically conductive material, in particular a conductive high consistency silicone rubber.

In another aspect, the plurality of legs is attached to the first longitudinal face of the base.

In another aspect, the electrode also comprises a joining element around which the plurality of legs extends, each leg being regularly spaced from its adjacent legs, said joining element being attached to the first longitudinal face of base.

In another aspect, the joining element presents a circle shape, the legs being disposed symmetrically around the base.

In another aspect, each leg comprises a first part and a second part forming an angle between 150° and 170° with each other.

In another aspect, the second part and the first part of the legs have the same length.

In another aspect, the legs extend from a side face of the base.

In another aspect, the legs comprise a curvature such that the symmetric legs respective to the longitudinal axis of base form a continuous arc.

In another aspect, the arc comprises an angle less than 180°.

In another aspect, the legs are longitudinally disposed along an edge of the first longitudinal face of the base.

In another aspect, the electrode further comprises a plug able to solidarize said electrode to a wearable assembly able to be worn on the user's head, said plug extending from the base.

In another aspect, the plug is able to transmit measured signals.

The present invention also relates to a wearable assembly comprising at least an electrode as described below, wherein the wearable assembly is able to exert a pressure on the electrode against the user's head when said wearable assembly is worn by the user, such that the electrode is able to be in contact with the user's scalp.

In another aspect, the electrode is removable from said wearable assembly.

The present invention also relates to a system comprising a wearable assembly, wherein the electrode is a first electrode, the system further comprising a plurality of electrodes assembled to said wearable assembly.

In another aspect, the electrodes of the plurality of electrodes differ from each other by at least one of the following parameters:
the size of the cross-section at the first extremities of the legs,
the size of the cross-section at the second extremities of the legs,
a value of the angle between the legs and the base.

BRIEF DESCRIPTION OF THE DRAWINGS

Other features and advantages of the invention will be apparent from the following detailed description of example embodiments and from the attached drawings, in which:

FIG. 1 is an isometric view of a first embodiment of an electrode,

FIG. 2 is a cross sectional view along the transversal axis of an electrode according to the first embodiment, FIG. 3 is a cross sectional view along the longitudinal axis of an electrode according to the first embodiment, FIG. 4 is an isometric view of another electrode according to first embodiment, FIG. 5 is a cross sectional view along the longitudinal axis of an electrode represented FIG. 4, FIG. 6 is a cross sectional view along the transversal axis of an electrode represented FIG. 4, FIG. 13 is an isometric view of a third embodiment of an electrode, FIG. 14 is a cross sectional view along the transversal axis of an electrode according to the third embodiment, FIG. 15 is a cross sectional view along the longitudinal axis of an electrode according to the third embodiment, FIG. 16 is an isometric view of a fourth embodiment of an electrode, FIG. 17 shows an electrode according to the fourth embodiment view from the above, FIG. 18 is a cross sectional view along the transversal axis of an electrode according to the fourth embodiment.

DESCRIPTION OF THE PREFERRED EMBODIMENTS

Figure 7:
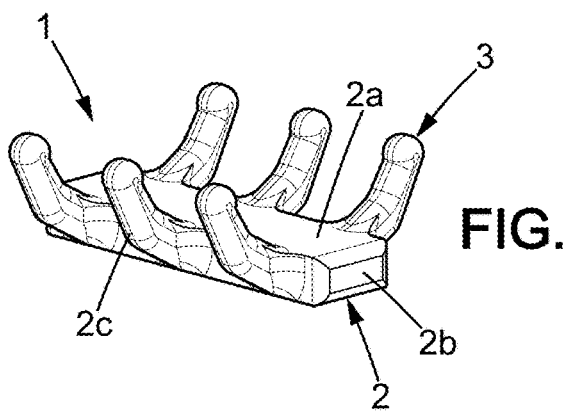
FIG. 7 is an isometric view of a second embodiment of an electrode.
Figure 8:
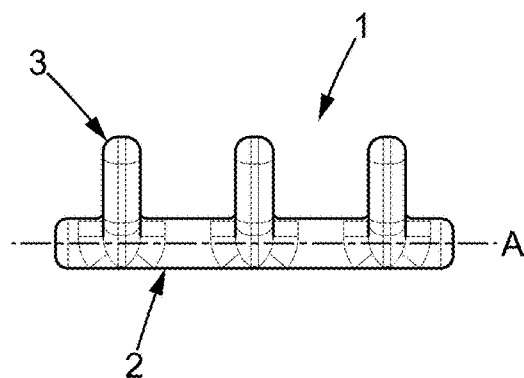
FIG. 8 is a cross sectional view along the longitudinal axis of an electrode according to the second embodiment.
Figure 9:
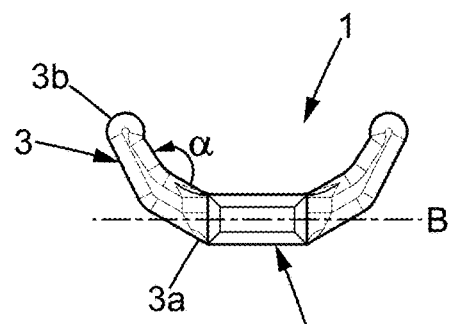
FIG. 9 is a cross sectional view along the transversal axis of an electrode according to the second embodiment.
Figure 10:
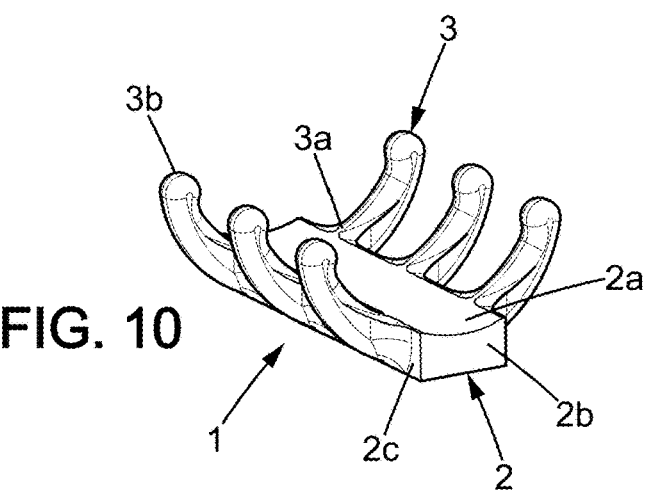
FIG. 10 is an isometric view of another electrode according to second embodiment.
Figure 11:
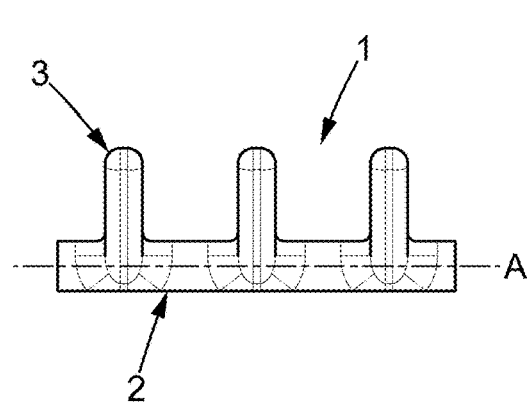
FIG. 11 is a cross sectional view along the longitudinal axis of an electrode represented FIG. 10.
Figure 12:
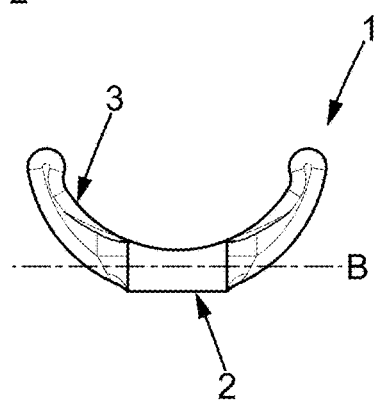
FIG. 12 is a cross sectional view along the transversal axis of an electrode represented FIG. 10.

Below is a detailed description of several embodiments of the invention, with examples and with references to the drawings.

Referring to FIGS. 1 to 6, one exemplary embodiment of an electrode 1 according to the present invention includes a base 2 and a plurality of legs 3.

The base 2 has for example a cuboid shape, such that it comprises six faces including a first and a second longitudinal faces 2a extending in a longitudinal direction A, two lateral faces 2b extending in a transversal direction B and a first and a second side faces 2c extending in the longitudinal direction A.

The legs 3 are for example attached to and extend from the first longitudinal face 2a of base 2.

In the following description, the electrode 1 is described considering that the electrode 1 is disposed in such a way that the electrode 1 lays on its second longitudinal face 2b, parallel to the ground, the legs 3 extending upwards. The electrode 1 is disposed in such a way that the first longitudinal face 2a and the legs 3 are directed to the skin of the user, or "the scalp".

The terms "up", "low" are used in reference with this spatial arrangement, regardless of the actual orientation of the electrode upon use.

The legs 3 are for example attached to base 2 by means of a joining element 4. The joining element 4 can have a circular shape, the legs 3 being integral with the joining element 4 around its circumference. The joining element 4 is attached to the first longitudinal face 2a of base 2.

Although the joining element 4 is depicted as circular or semicircular in FIGS. 1 and 4, the joining element 4 may be of any shape.

The electrode 1 may comprise between three and eight legs 3. The legs are for example disposed around the joining element 4 in such a way that each leg 3 is equally spaced from its adjacent legs 3. The legs 3 comprises a first extremity 3a that is attached to base 2 and the joining element 4, and a second extremity 3b opposite to first extremity 3a.

The legs 3 may be formed with a flexible material, such that when they are pressed against the user's head, to acquire EEG signals, the legs 3 elastically flex and their second extremity 3b slides on the user's head. The flexibility and the shape of the legs assure the penetration of the legs 3 through the hair of the user, such that the second extremity 3b is able to be directly in contact with the scalp of the user.

When a pressure is applied, generally to base 2, the legs 3 elastically flex and the second extremity 3b of the legs 3 slide against the user's head, through the hair. The base 2 may be able to absorb the pressure applied against the scalp of the user, such that the user does not feel any pressure at the level of the extremities of the legs 3, which could be painful.

To enhance the sliding of the second extremities 3b, the legs 3 may be attached to base 2 such that they form an angle between 20° and 80° with the first longitudinal face 2a of base 2.

The flexible material may also allow the shortening of the angle while the sliding of the second extremities 3b of the electrode 1.

The material used for the legs 3 may also be electrically conductive to acquire rugged bio-signals. The material may be an electrically conductive elastomer, for example, the material is a conductive—high consistency silicone rubber.

Generally, the high consistency silicone rubber (or "HCR") is able to deform and recover it original shape, which renders the legs 3 unbreakable. The high consistency silicone rubber contains polymers with a high molecular weight and long polymer chains. It has a high degree of elasticity and presents advantageous electrical attributes.

Alternatively, base 2 and joining element 4 may also be made with an electrically conductive material such as the one used for the legs 3.

To improve the quality of the measured bio-signals, the second extremity 3b of the legs 3 is for example covered with a highly electrically conductive material, for example a mixture of silver and silver chloride (or "Ag/AgCl") that can adhere to silicone rubber surfaces.

An individual leg 3 includes a first part 3c and a second part 3d, the first part being the closest from base 2.

In the embodiment illustrated FIGS. 1 to 3, the lower and second parts 3c, 3d are aligned.

Alternatively, the first part 3c may form an angle with the second part 3d, called the elbow angle α. It has been found that the elbow angle α between the lower and second parts 3c, 3d enhanced the hair penetration of the leg 3. The elbow angle α is for example comprised between 150° and 170°, depending of the structure of the electrode 1.

The upper and first parts 3c, 3d of legs 3 may have the same length.

To enhance the penetration of the legs through the hair of the user, the cross-section of the first extremity 3a is larger than the cross-section of the second extremity 3b.

The size of the cross-section at the extremities 3a, 3b, especially first extremity 3a, can be chosen depending of the type of hair of the user. For example, if the user has thin and/or short hair, the cross-section of the first extremity 3a does not need to be really large. In contrary, for thick or curled hair, the cross-section of the first extremity 3a should be larger.

As an exemplary illustration, the width of the cross-section near the first extremity 3a may be comprise between 2 and 2.5 millimeters (mm) whereas the width of the cross-section near the second extremity 3b can be comprise between 1.1 and 2 mm.

FIGS. 7 to 12 illustrate a second embodiment of the present invention.

The electrode 1 comprises a base 2 and a plurality of legs 3 attached to base 2. Although the electrode depicted in FIGS. 7 to 9 comprises six legs 3, the electrode may comprise less or more legs 3. For example, the number of legs 3 can be comprise between three or eight.

If the electrode 1 comprises less than three legs, the measured bio-signals may not be rugged enough. In contrary, if the electrode 1 comprises more than eight legs, the size of the electrode 1 should be much larger to receive all the legs, while keeping the length and the size of the cross-sections of the legs 3.

Base 2 still may be of cuboid shape. The legs 3 are for example directly attached to the side faces 2c of base 2 such that there is no more need of using a joining element 4. The legs 3 are for example symmetrically attached to base 2 and the legs 3 attached to a side face 2c of base 2 face the legs attached to the other side face 2c. The legs 3 may be regularly disposed along each side faces 2c.

The reparation of the legs 3 on the side faces 2c improves the comfort of the electrode 1 when it is applied against the user's head. The base 2 may absorb all of the pressure applied to the electrode to allow the contact with the user's scalp.

The legs 3 may be made with a flexible electrically conductive material, such as conductive high consistency silicone rubber, as depicted in relation with first embodiment. This particularly allows the legs 3 to be flexible, such that when the electrode is applied against the user's head, the legs 3 elastically flex and their second extremities 3b are able to slide against the user's head, through the hair, to be in contact with the scalp of the user.

The second extremities 3b of the legs 3 may also be covered with a high electrically conductive material, for example a mixture of silver and silver chloride, to enhance the acquisition of the EEG signals. Since legs 3 are entirely made with conductive materials, more precisely the mixture of silver and silver chloride and high consistency silicone rubber, the electrode 1 is able to acquire rugged EEG signals.

Alternatively, base 2 may also be made with conductive high consistency silicon rubber, such that the entirety of the electrode 1 is electrically conductive. This may enhance the quality of the acquired EEG signals.

The legs 3 can comprise two parts, as described above, that is to say a first part 3c and a second part 3d, which form an elbow angle α with each other. The elbow angle α is for example comprised between 170 and 180°.

The upper and first parts 3c, 3d may have the same length.

Alternatively, the legs 3 do not present an elbow angle. In this case, the legs 3 present a curvature. The first longitudinal face 2a of base 2 may be integrated in the curvature made by the legs 3. It is shown in the cross sectional view of FIG. 12. The inner surfaces of the legs 3 facing each other, i.e. the surface directed towards base 2, and the portion of the first longitudinal face 2a of base 2 are in continuation of each other such that they generally form an arc.

A first inner diameter can thus be defined as being the diameter of the arc defined by the inner surfaces of legs 3. An outer diameter can also be defined as being the diameter of the arc defined by the outer surfaces of legs 3.

The inner diameter is for example comprised between 13 and 23 mm, whereas the outer diameter may be comprised between 15 and 25 mm, such that the diameter of the cross section of the legs 3 is generally comprised between 1 and 2 mm.

The cross-section of the legs 3 at their first extremities 3a is larger than the cross-section of the legs 3 at their second extremities 3b Making the first extremities 3a of the legs thicker than the second extremities 3b increases the rigidity of the legs 3 for penetration in long or thick hair.

Figure 19:
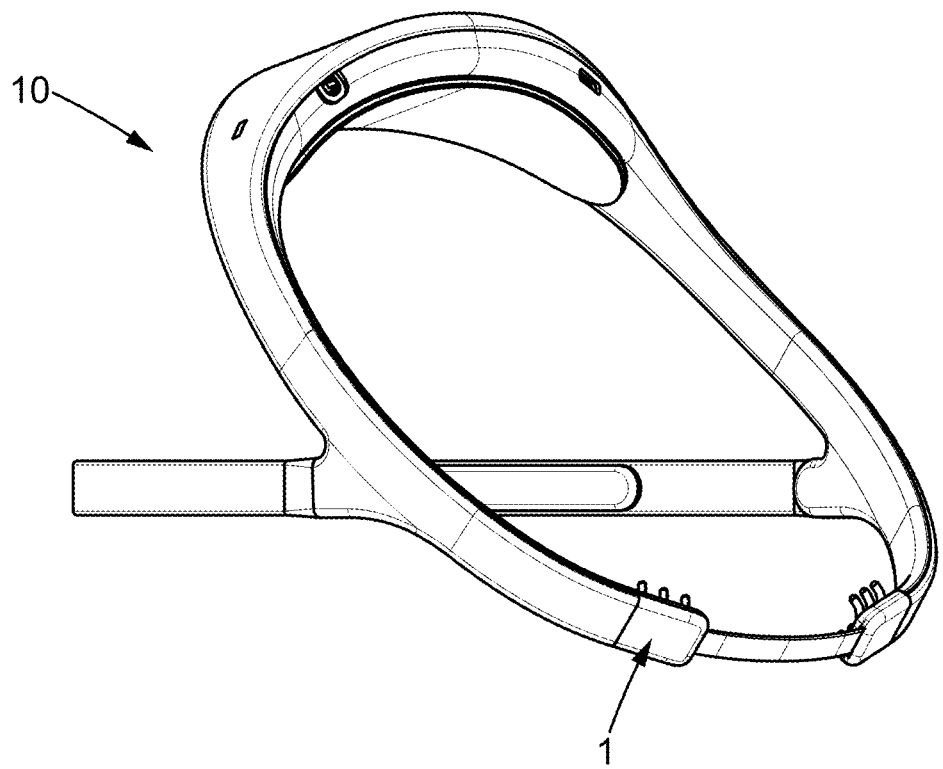
FIG. 19 is a wearable assembly comprising an electrode according to any of the fourth embodiments.

As illustrated in FIG. 19, the electrode can be part of a wearable assembly, which is further described below. When the wearable assembly is worn by a user, the electrode, and more particularly the base 2, is applied against the user's head, near the occipital region of the head. Then, when the wearable assembly is worn by the user, the legs 3 of the electrode 1 extend in a parallel way to the implantation direction of the hair of the user. In other words, the reparation of the legs of the embodiments illustrated FIGS. 7 to 12, symmetrically with respect to the side faces 2c of the base 2 and each extending perpendicularly to the base 2, allows the legs to be aligned with the implantation direction of the hair of the user in a configuration of use.

Hence, when the wearable assembly 10 is worn, the tips of the legs 3 are already in contact with the user's head without a necessity of applying a great pressure on the electrode. This increases significantly the comfort of the user when using the electrode.

Moreover, because of the particular geometry of the electrode, the legs 3 can be made with a highly flexible material. This particularly allows the legs 3 to be very flexible, such that, when the electrode is applied against the user's head, the legs 3 elastically flex and their second extremities 3b are able to slide even more against the user's head, through the hair. In another hand, since the material is very flexible, the user does not feel any pressure at the tips of the legs, which could be painful and uncomfortable.

FIGS. 13 to 15 illustrate a third embodiment of the present invention wherein parts which are equivalent to or identical to those in the above-mentioned embodiments are given the same reference numbers, and the description thereof is omitted. Only the features thereof are described below.

In the embodiment shown on FIGS. 13 to 15, the legs 3 are attached to and extend from base 2, more precisely, the legs 3 are attached to and extend from the first longitudinal face 2a of base 2.

The legs 3 may present curvature. More precisely, the legs 3 extend transversally to the first longitudinal face 2a such that the electrode is generally curved shaped in cross sectional view, as illustrated FIG. 14.

The first extremities 3a of the legs 3 may still be thicker than the second extremities 3b of legs 3, such that the legs are able to penetrate through the hair of the user when the electrode 1 is applied against the user's head.

FIGS. 16 to 18 show a fourth embodiment of the present invention wherein parts which are equivalent to or identical to those in the above-mentioned embodiments are given the same reference numbers, and the description thereof is omitted. Only the features thereof are described below.

In this embodiment, the legs 3 are attached to and extend from the first longitudinal face 2a of base 2. The electrode illustrated FIGS. 16 to 18 comprises six legs, although it can comprise more or less legs, for example between three and eight.

The legs 3 may be disposed symmetrically along each edge of the first longitudinal face 2a of base 2. They may be regularly spaced from each other, a leg 3 being in front of another leg 3.

By way of a non-limiting example, the legs 3 are longitudinally spaced from each other by a distance between 4 and 6 mm, for example 5.5 mm.

The legs 3 present a cross-section at their first extremities 3a larger than the cross-section at their second extremities 3b. For example, the diameter of the cross-section at the first extremities 3a is between 3 and 4 mm, whereas the diameter of the cross-section at the second extremities 3b of the legs is between 1 and 2 mm.

The first extremities 3a of the legs 3 extend along the first longitudinal face 2a of base 2, such that the first extremities 3a of two facing legs 3 touch each other.

For example, the second extremities 3b of two facing legs 3 are spaced by a distance comprised between 10 and 15 mm, for example 12 mm.

The legs 3 are generally curved, such that the inner surfaces of the legs 3 facing each other are in continuation of each other and form an arc. The angle of the arc from a second extremity 3b of a leg 3 to the other extremity of the facing leg 3 is less than 180° to facilitate the penetration of the legs 3 through the hair of the user. For example, the angle is comprised between 140° and 150°.

The legs 3 are made with a flexible and electrically conductive material, for example conductive high consistency silicone rubber. The second extremities 3b of legs 3 may be covered with a higher electrically conductive material, for example a mixture of silver and silver chloride.

As described above, the flexibility of the legs 3 allows the second extremities 3b to slide on the user's head, through the hair, such that the high conductive material is in contact with the scalp of the user to enhance the quality of the acquired signals.

Moreover, the relative thinness of the second extremities 3b enhances the comfort of the electrode 1 when it is applies against the user's scalp. Indeed, the electrode 1 is for example intended to be worn by the user during a period of sleep.

The electrode 1 is for example integrated in a wearable assembly 10 intended to be worn on the head of the user.

The electrode 1 may comprise a plug 5 made of an electrically conductive material, such as metal, or an alloy of metals. The electrode 1 may also comprise two rails 6, extending longitudinally from each side faces 2c of base 2.

For example, the rails 6 and the plug 5 form a whole and one piece, around which base 2 and legs 3 are overmolded.

To integrate the electrode 1 in a wearable assembly 10, a support 7 may be provided. The support for example comprises two grooves in which the rails 6 are inserted by sliding. The transversal face 2b of base 2 form a mechanical stop. When inserted, the support 7 may cover the second longitudinal face 2b and the side faces 2c of the base 2.

The electrode 1 and the support 7 are attached to the wearable assembly 10 by inserting the plug 5 in the wearable assembly 10. The plug 5 is able to be tightened in wearable assembly 10 by means of an insert (not shown) comprised in the wearable assembly 10. The insert may be able to deform elastically so as to maintain the plug 5 in the wearable assembly 10.

The plug 5 may also connect the electrode 1 to electronics comprised in the wearable assembly, which monitor the bio signals measured by the electrode 1. The connection is for example made by the means of the insert connected to a wire comprised in the wearable assembly 10, the insert making the connection between the wire and the plug 5.

The electrode 1 may be removable from the wearable assembly 10, such that the user may interchange the electrode in function of the type of his hair. To remove the electrode 1, the user pulls out the electrode 1 to unclench the plug 5.

Figure 20:
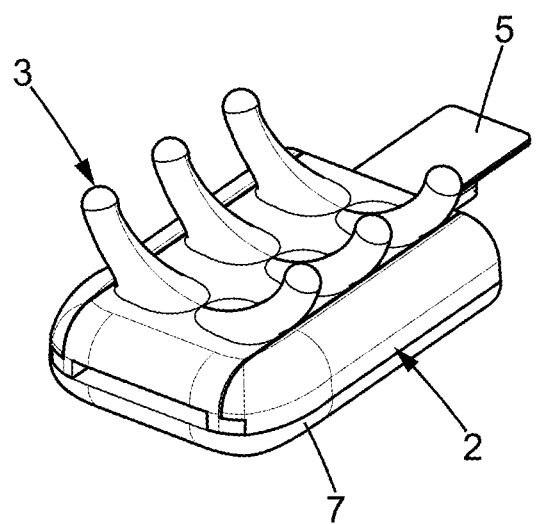
FIG. 20 is an isometric view of an electrode according to the fourth embodiment attached to a support able to solidarize the electrode to the wearable assembly.
Figure 21:
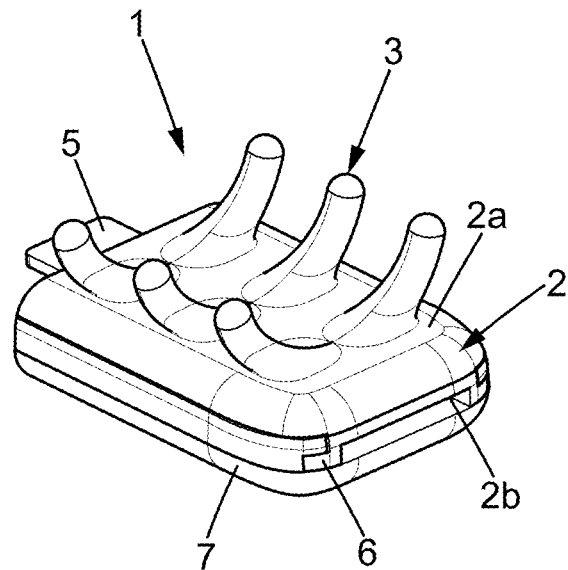
FIG. 21 is an isometric view of an electrode according to the fourth embodiment attached to a support able to solidarize the electrode to the wearable assembly.

FIG. 21 shows an alternative embodiment of the embodiment illustrated on FIG. 20. The electrode is attached to the support 7 by means of rails 6. The rails may be longitudinally attached to the second longitudinal faces 2b of the electrode 1. As described above, the support 7 comprises two grooves in which the rails 6 are inserted by sliding. When inserted, the support 7 may only cover the second longitudinal face 2b of the electrode.

Figure 22:
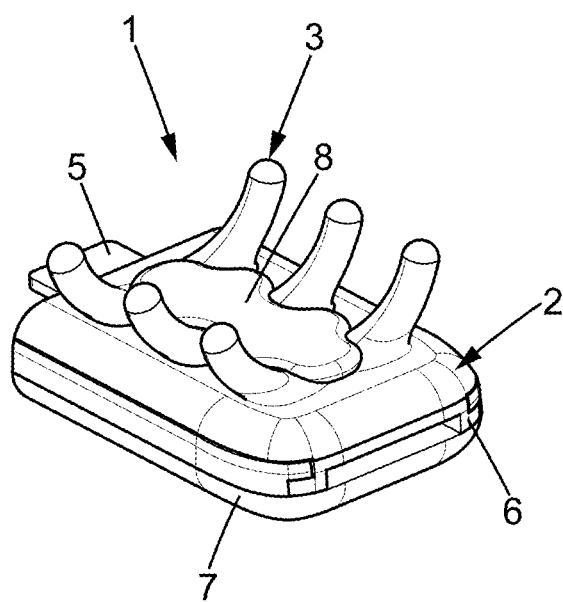
FIG. 22 is an isometric view of an alternative embodiment of an electrode according to the fourth embodiment, attached to a support able to solidarize the electrode to the wearable assembly.

FIG. 22 shows an alternative embodiment of the embodiment illustrated on FIG. 21. The first longitudinal face of the base 2 of the electrode 1 may comprise a raised area 8. The raised area 8 extends for example from one leg 3 to another, between the first extremities 3a of each leg 3.

The width of the raised area 8 may be comprised between 0.7 and 2 millimeters. The raised area 8 may enhance the comfort of the electrode 1 when it is worn by a user. The type of electrode 1 depicted on FIG. 22 is for example particularly adapted for a user having a low hair density.

REFERENCES

| | | |
|---|---|---|
| electrode | | 1 |
| base | | 2 |
| first and second longitudinal faces | | 2a |
| lateral face | | 2b |
| side face | | 2c |
| leg | | 3 |
| first extremity | | 3a |
| second extremity | | 3b |
| first part | | 3c |
| second part | | 3d |
| joining element | | 4 |
| plug | | 5 |
| rail | | 6 |
| support | | 7 |
| raised area | | 8 |
| wearable assembly | | 10 |

The invention claimed is:

1. An electrode for acquiring electroencephalogram signals of a user, comprising:
a base and a plurality of elastically flexible legs extending from said base at first extremity, said elastically flexible legs comprising a second extremity covered with an electrically conductive material, said second extremity comprising a smaller cross-section than the first extremity of said elastically flexible legs such that the elastically flexible legs are able to penetrate through hair of the user and wherein the elastically flexible legs are able to elastically flex such that, when the electrode is applied on a head of a user, the electrically conductive material of the second extremity is in contact with a scalp of the user,
wherein the base is of cuboid shape having two side faces, the elastically flexible legs being directly attached to the side faces of the base, the elastically flexible legs being symmetrically attached to the base with respect to a longitudinal axis (A), the elastically flexible legs attached to a side face of the base facing the elastically flexible legs attached to the other side face of the base.

2. The electrode according to claim 1, wherein at least one of the elastically flexible legs forms an angle comprised between 20° and 80° with a first longitudinal face of the base.

3. The electrode according to claim 1, wherein the elastically flexible legs and/or the base are made of electrically conductive material.

4. The electrode according to claim 3, wherein the elastically flexible legs and/or the base are made of a conductive high consistency silicone rubber.

5. The electrode according to claim 1, wherein the elastically flexible legs comprise a curvature such that the elastically flexible legs respective to the longitudinal axis (A) of base form a continuous arc.

6. The electrode according to claim 1, further comprising: a plug able to solidarize said electrode to a wearable assembly able to be worn on the head of the user, said plug extending from the base.

7. The electrode according to claim 1, wherein each of the elastically flexible legs forms an angle comprised between 20° and 80° with a first longitudinal face of the base.

8. The electrode according to claim 1, wherein at least one of the elastically flexible legs forms an angle comprised between 20° and 60° with a first longitudinal face of the base.

9. An assembly, comprising:
a wearable assembly configured to be worn on a head of a user,
the wearable assembly comprising an electrode for acquiring electroencephalogram signals of a user, comprised of
a base and a plurality of elastically flexible legs extending from said base at first extremity, said elastically flexible legs comprising a second extremity covered with an electrically conductive material, said second extremity comprising a smaller cross-section than the first extremity of said elastically flexible legs such that the elastically flexible legs are able to penetrate through hair of the user and wherein the elastically flexible legs are able to elastically flex such that, when the electrode is applied on a head of the user, the electrically conductive material of the second extremity is in contact with a scalp of the user,
the base being of cuboid shape having two side faces, the elastically flexible legs being directly attached to the side faces of the base, the elastically flexible legs being symmetrically attached to the base with respect to a longitudinal axis (A), the elastically flexible legs attached to a side face of the base facing the elastically flexible legs attached to the other side face of the base,
wherein the wearable assembly is configured to exert a pressure on the electrode against the head of the user when said wearable assembly is worn by the user such that the electrode contacts with the scalp of the user.

10. The wearable assembly according to claim 9, wherein the electrode is removable from said wearable assembly.

11. A system comprising a wearable assembly according to claim 9, wherein the electrode is a first electrode, the system further comprising a plurality of electrodes assembled to said wearable assembly.

12. The system according to claim 11, wherein the electrodes of the plurality of electrodes differ from each other by at least one of the following parameters:
the size of the cross-section at the first extremities of the elastically flexible legs,
the size of the cross-section at the second extremities of the elastically flexible legs,
a value of the angle between the elastically flexible legs and the base.

* * * * *